United States Patent
Chalmers (10) Patent No.: US 9,019,484 B2
(45) Date of Patent: Apr. 28, 2015

(54) COMBINING NORMAL-INCIDENCE REFLECTANCE AND TRANSMITTANCE WITH NON-NORMAL-INCIDENCE REFLECTANCE FOR MODEL-FREE CHARACTERIZATION OF SINGLE-LAYER FILMS

(75) Inventor: Scott A. Chalmers, San Diego, CA (US)

(73) Assignee: Filmetrics, Inc., San Diego, CA (US)

( * ) Notice: Subject to any disclaimer, the term of this patent is extended or adjusted under 35 U.S.C. 154(b) by 632 days.

(21) Appl. No.: 13/253,830

(22) Filed: Oct. 5, 2011

(65) Prior Publication Data

US 2012/0176604 A1      Jul. 12, 2012

Related U.S. Application Data (60) Provisional application No. 61/390,338, filed on Oct. 6, 2010.

(51) Int. Cl.
*G01N 21/00*      (2006.01)
*G01B 11/06*      (2006.01)
*G01N 21/55*      (2014.01)
*G01N 21/59*      (2006.01)
*G01N 21/84*      (2006.01)

(52) U.S. Cl.
CPC ............ *G01B 11/0625* (2013.01); *G01N 21/55* (2013.01); *G01N 21/59* (2013.01); *G01N 21/8422* (2013.01)

(58) Field of Classification Search
CPC ..... G01B 11/0625; G01N 21/55; G01N 21/59
USPC ......... 356/432, 435, 481, 517, 504, 445–448, 356/451
See application file for complete search history.

(56) References Cited

U.S. PATENT DOCUMENTS

| | | | | |
|---|---|---|---|---|
| 5,889,592 | A * | 3/1999 | Zawaideh | 356/504 |
| 6,411,385 | B2 * | 6/2002 | Aspnes et al. | 356/369 |
| 6,583,875 | B1 * | 6/2003 | Wei et al. | 356/369 |
| 6,731,386 | B2 * | 5/2004 | Dautartas et al. | 356/369 |
| 6,774,997 | B2 * | 8/2004 | Rosencwaig et al. | 356/369 |
| 6,963,401 | B2 * | 11/2005 | Opsal et al. | 356/369 |
| 7,349,079 | B2 * | 3/2008 | Zhao et al. | 356/128 |
| 7,463,355 | B1 * | 12/2008 | Zawaideh | 356/364 |
| 7,599,072 | B2 * | 10/2009 | Kim et al. | 356/601 |

* cited by examiner

Primary Examiner — Kara E Geisel
Assistant Examiner — Maurice Smith
(74) Attorney, Agent, or Firm — IPR Law Group, PC (57) ABSTRACT

Optical systems and methods are described that provide greater solving power for thin-film measurements in general, and provide a unique model-free solution for single-layer films in particular.

70 Claims, 6 Drawing Sheets

FIG. 6

COMBINING NORMAL-INCIDENCE REFLECTANCE AND TRANSMITTANCE WITH NON-NORMAL-INCIDENCE REFLECTANCE FOR MODEL-FREE CHARACTERIZATION OF SINGLE-LAYER FILMS

RELATED APPLICATION

This application claims the benefit of U.S. Patent Application No. 61/390,338, filed Oct. 6, 2010.

TECHNICAL FIELD

This invention relates generally to the field of thin-film metrology.

BACKGROUND

Many products use film coatings to modify the characteristics of the product's surface. Polycarbonate eyeglass lenses, for example, use a film "hard coat" to protect against scratching Film thicknesses can range from 0.0001 micron (um) to hundreds of microns, depending upon the application. It is usually important to control the film's thickness and its composition, whether to optimize the performance of the film or simply to minimize the amount of film material that is used.

Spectral reflectance is common method for measuring film thickness, as well as for measuring other film properties such as optical constants. Spectral reflectance methods first measure the amount of light reflected off of or transmitted through the film sample (which contains the film or films of interest, along with any other films or substrate that might be present) over a range of wavelengths, and then analyze this reflectance spectrum to determine the film's properties.

The term "spectral reflectance" (SR) is used herein to refer to both reflectance and transmittance measurements, at both normal and non-normal incident angles, where polarization changes neither occur nor are detected. This distinguishes SR from ellipsometry, which, in contrast, is concerned primarily with polarization changes induced by the sample. For examples and general reference, see "Spectroscopic Ellipsometry and Reflectometry: A User's Guide" by Tompkins and McGahan, John Wiley & Sons, 1999. Companies such as Filmetrics, Inc. of San Diego, Calif. manufacture such spectral reflectance systems.

The analysis of a measured SR spectrum typically consists of comparing it to a set of theoretical SR spectra that are generated based on the sample's expected properties. Some of these properties are known and thus fixed when generating the theoretical spectra, while others are unknown (i.e. they are being measured) and assume a range values corresponding to those anticipated in the sample. The values of the unknown properties that result in the theoretical spectrum that most closely matches the measured spectrum are then taken to most closely represent the actual properties of the sample; these values are thus the "measured" values.

There are a number of film properties that might need to be measured. These include the film's thickness, roughness, and composition. The composition, which may be homogenous or not, is usually described in terms of the two optical constants: refractive index (n) and extinction coefficient (k). Both n and k are functions of wavelength, which means that, when measured, they must be determined for each discrete wavelength that comprises the SR spectrum. If the number of discrete wavelength data points in the SR spectrum is represented as i, then the number of values of n that need to be determined is i, as is the number of values of k that need to be determined. Even assuming a smooth homogeneous film (i.e. no roughness or compositional grading) of thickness d, the number of free (solved for) parameters is 2i+1 (n and k and thickness), whereas the number of known parameters (R) is only i. Since more known parameters than unknown parameters are required to be able to solve uniquely for a film's properties, either d and k much be known (the latter often=0) to solve for n, or, as is more often the case, n and k are known (or at least assumed) and d is solved for.

The usual method of simultaneously solving for a film's d, n, and k with only i reflectance data points is to use a mathematical model to estimate the wavelength dependence of the film's n and k. Such a model (e.g., Lorentz, Harmonic Oscillator) can reduce the number of parameters required to describe n and k down from 2i to between one and a few dozen. This method works acceptably for films whose n and k are well-described by such a model. However, for many films, this method can result in a loss in accuracy (especially for models with fewer parameters) and solving robustness (especially for models with larger numbers of parameters). Additionally, resorting to mathematical models for n and k is a challenge in the course of day-to-day measurements—the complexity of the models means that the skill of highly-trained experts are often required whenever a new film stack is encountered. This is not usually the case in a "model-free" situation.

A method in the art for acquiring an additional i known parameters (i.e. one additional known parameter per wavelength data point) is to combine transmittance (T) with reflectance measurements, for a total of 2i known parameters. For a smooth (non-scattering) film, this is still fewer than the required 2i+1 unknown parameters (n and k and thickness), so either d must be known or a model used for n and k. Note that when k=0 there is no absorption and T=1−R, so that there are only really i known and i+1 unknown parameters, so that T adds no additional information in this case.

INCORPORATION BY REFERENCE

Each publication, patent, and/or patent application mentioned in this specification is herein incorporated by reference in its entirety to the same extent as if each individual publication, patent and/or patent application was specifically and individually indicated to be incorporated by reference.

DETAILED DESCRIPTION

Embodiments described herein provide SR optical configurations for use in determining a relatively greater number of film properties than can be determined by combining single-angle reflectance and transmittance measurements, whether n and/or k are solved uniquely and exactly or with the aid of models. The embodiments herein also describe SR optical configurations that are used to determine all film properties (n and k and thickness) uniquely and exactly, i.e., without the aid of models for n and/or k.

In the following description, numerous specific details are introduced to provide a thorough understanding of, and enabling description for, embodiments of the reflectance systems. One skilled in the relevant art, however, will recognize that these embodiments can be practiced without one or more of the specific details, or with other components, systems, etc. In other instances, well-known structures or operations are not shown, or are not described in detail, to avoid obscuring aspects of the disclosed embodiments.

Figure 1:
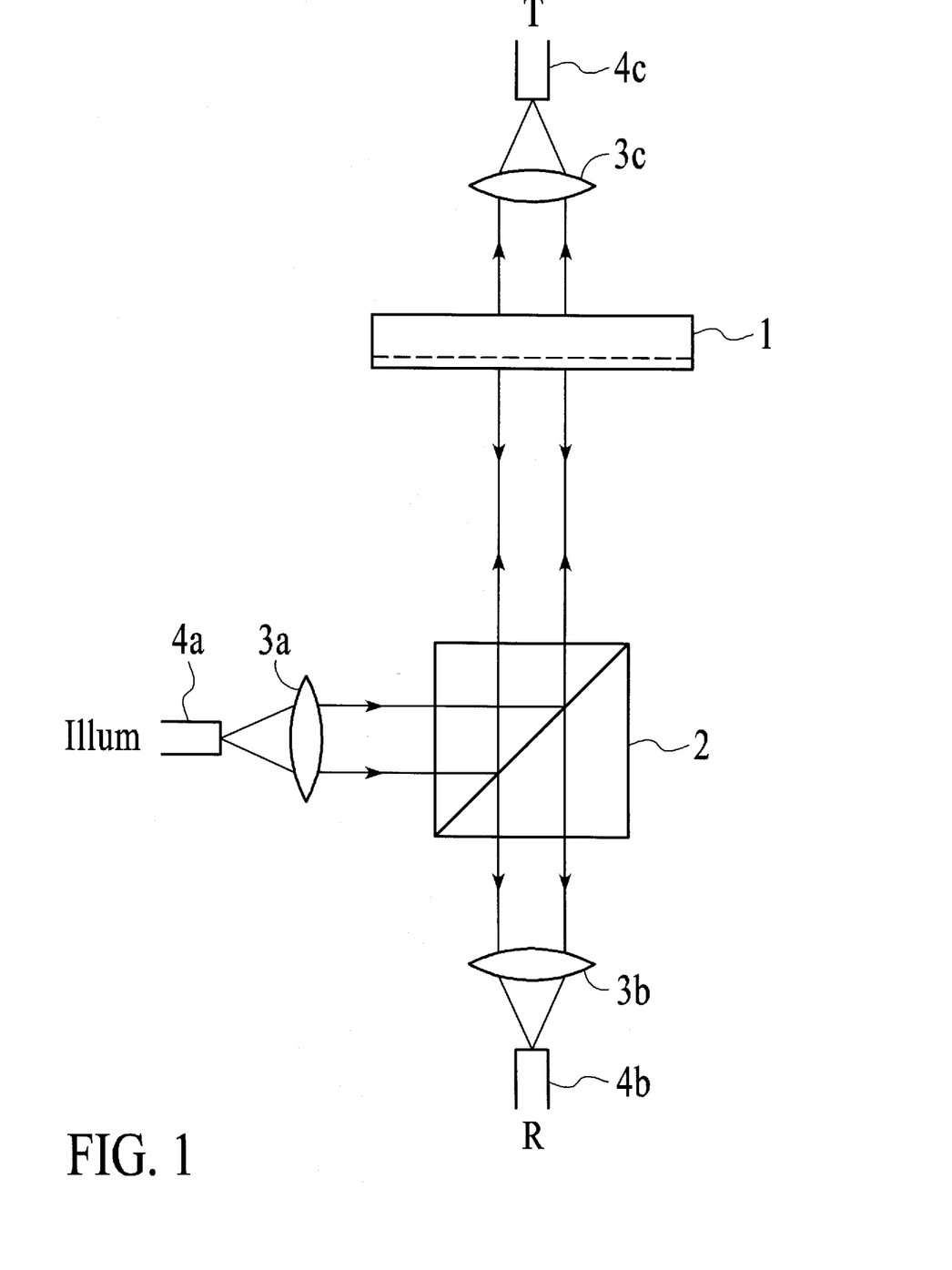
FIG. 1 is a schematic of a system for making reflectance and transmittance measurements, under an embodiment.

FIG. 1 shows an optical configuration for measuring R and T normal to the sample 1, which has a film coating on the bottom side. Illumination light comes from the left of beamsplitter 2, in this embodiment exiting from a fiber 4a. The illumination light is collimated by lens 3a before entering the beamsplitter, which directs the illumination light toward the sample. The sample reflects a portion of this light back down through the beamsplitter to the focusing lens 3b and reflectance collection fiber 4b. Some of the non-reflected light that strikes the sample transmits through to focusing lens 3c and transmittance collection fiber 4c.

Figure 2:
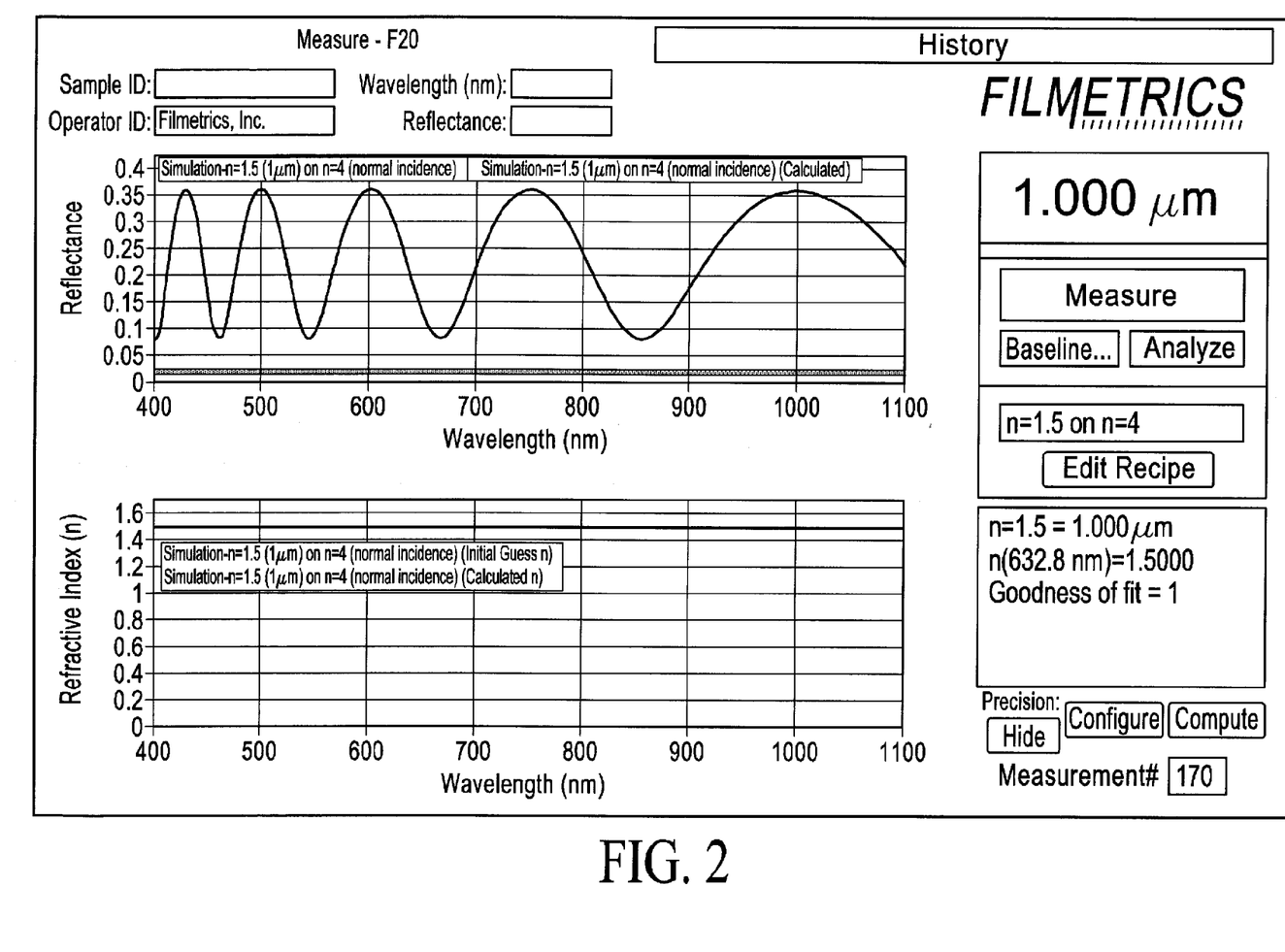
FIG. 2 shows the calculated normal-incidence reflectance spectra of a 1 um-thick n=1.5 film on an n=4 substrate.
Figure 3:
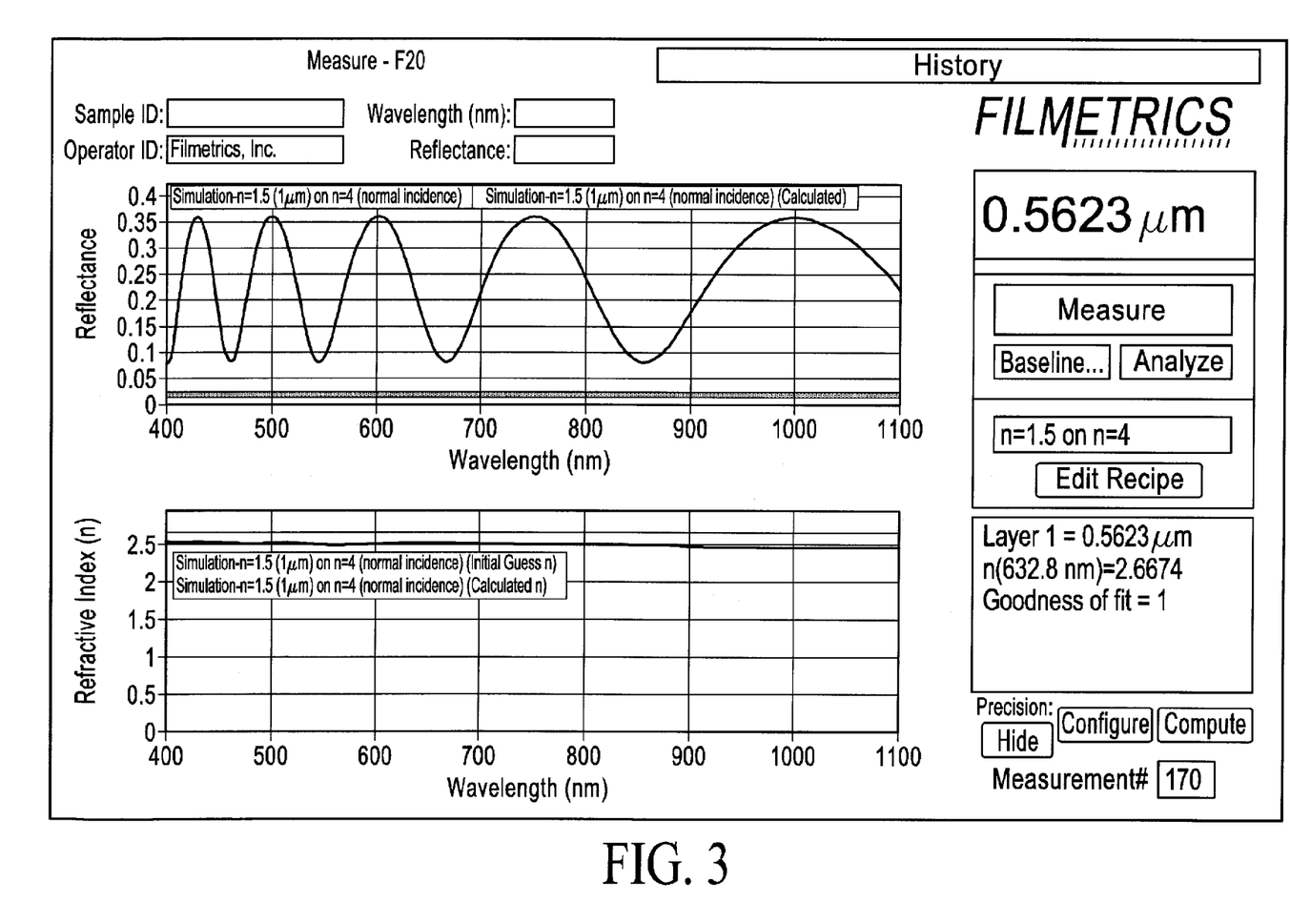
FIG. 3 shows the calculated normal-incidence reflectance spectra of a 1 um-thick n=1.5 film on an n=4 substrate, along with the calculated normal-incidence reflectance spectra of a 0.5623 um-thick n=2.6674 film on an n=4 substrate.

FIGS. 2 and 3 demonstrate that a unique solution for n and k and thickness d is not possible with normal-incidence R and T spectra alone. For simplicity it is assumed herein that k=0, and thus have not included the T spectrum (which as discussed contains no additional information, since T=1−R in the absence of roughness and absorption). The film stack in this illustration is the common situation of a low-index (n=1.5) film on a high-index substrate (n=4), where the film has d=1 um. Only the film's characteristics, n and d, are considered unknown.

FIG. 2 shows the solution of n=1.5 and d=1 um, i.e., the calculated spectrum for n=1.5 and d=1 um is overlaid on the theoretical measured spectrum and found (by definition) to fit essentially perfectly (GOF, or goodness-of-fit, =1 in the figure). No other combination of theoretical n and d in the neighborhood of this solution results in nearly as good of a fit.

FIG. 3, however, shows a second combination of theoretical n and d that are farther away from the actual film properties that also result in an excellent fit (GOF=1), specifically n=2.6674 and d=0.5623 um. Therefore there are two equally good fits and two equally good solutions for n and d, and thus a unique solution is not possible. (It can be shown that two solutions for n are expected in the low-index film on high-index substrate case, and they are located on either side of the square root of the index of the substrate).

A measurement system of an embodiment includes a first light source that illuminates a film with first illumination having a first angle of incidence that is approximately normal to a film that covers at least a portion of a first side of a sample. A transmittance collection fiber collects transmitted light of the first illumination transmitted by the film, and a first collection fiber collects reflected light of the first illumination reflected by the film. A second light source illuminates the film with second illumination having a second angle of incidence that is approximately non-normal to the film, and a second collection fiber collects reflected light of the second illumination reflected by the film. A model-free method or application is used to uniquely and exactly determine at least one property of the film using data of the normal-incidence reflected light, the normal-incidence transmitted light, and the non-normal-incidence reflected light.

The spectral reflectance measuring methods of this measurement system embodiment comprise illuminating a film from a first angle of incidence that is approximately normal to the film and collecting normal-incidence reflected light from the film and normal-incidence transmitted light transmitted by the film. The film is also illuminated from a second angle of incidence that is approximately non-normal to the film, and non-normal-incidence reflected light is collected from the film. One or more properties of the film are determined using data of the normal-incidence reflected light, the normal-incidence transmitted light, and the non-normal-incidence reflected light in a model-free process or application.

Figure 4:
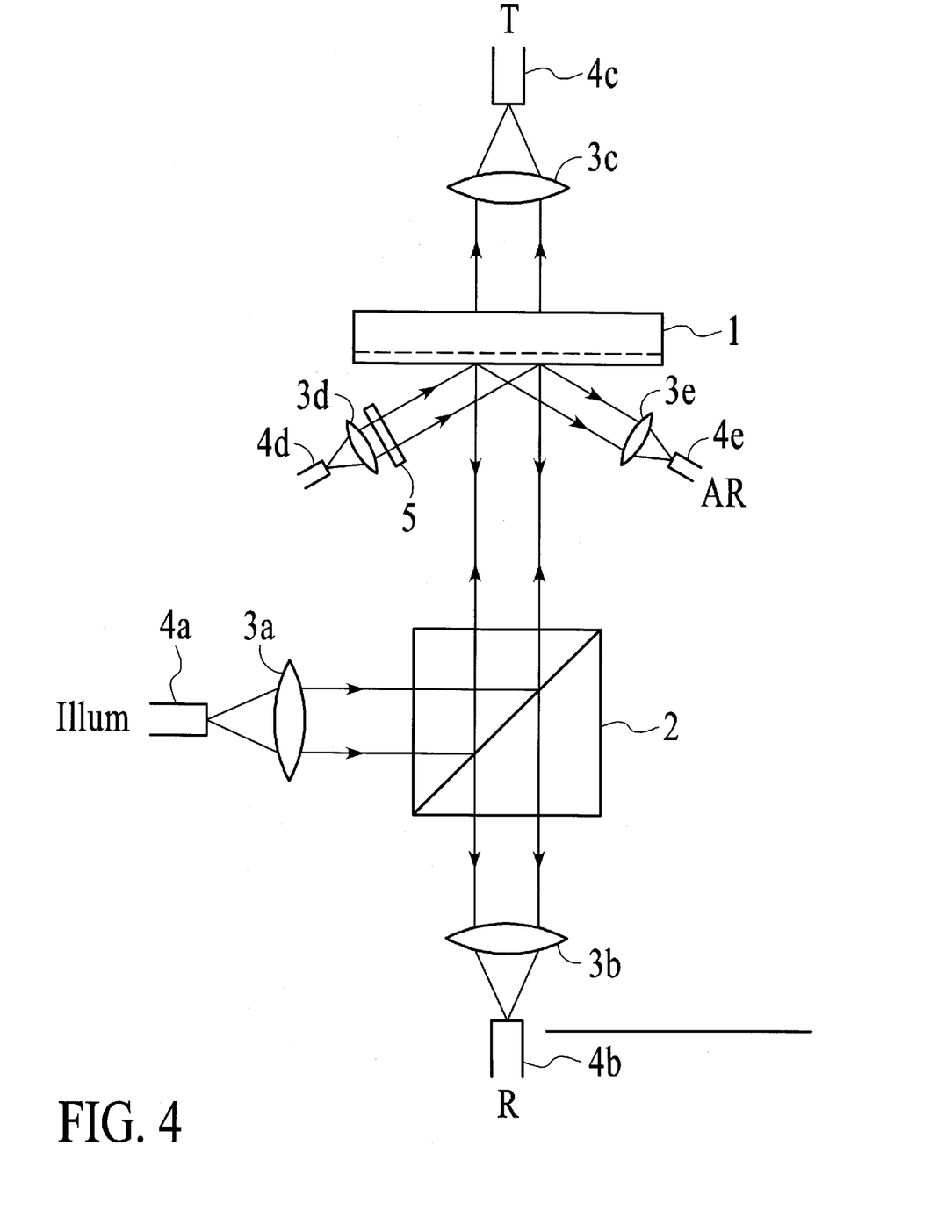
FIG. 4 is a block diagram of an apparatus for measuring film properties using non-normal incidence reflectance (i.e., angled reflectance (AR)) along with transmittance and/or normal-incidence reflectance, under an embodiment.

More particularly, FIG. 4 shows an apparatus for measuring film properties using transmittance, normal-incidence reflectance, and non-normal incidence reflectance (i.e., angled reflectance (AR)), under an embodiment. The apparatus includes a first light source 4a that, in an embodiment, is an optical fiber 4a. The light from the first light source 4a is collimated by a lens 3a, and directed by a beamsplitter 2 onto the sample 1, which has a film coating on the bottom side. Transmittance and normal-incidence reflectance data result from the illumination of the first light source.

The sample reflects a portion of the normal-incident illumination light back down through the beamsplitter 2 to a focusing lens 3b. The focusing lens 3b focuses the normal-incidence reflected light for collection by a reflectance collection fiber 4b. At least a portion of the non-reflected light that illuminates the sample is transmitted through the sample to focusing lens 3c, which focuses the transmitted light for collection by a transmittance collection fiber 4c.

The apparatus also includes a second light source 4d that is, for example, an optical fiber 4d. The light from the second light source 4d is collimated by a lens 3d and then directed to a polarizer 5. The polarizer polarizes the incident illumination light so that the electric field components are either parallel (TM polarized) or perpendicular (TE polarized) to the sample surface. This prevents the sample from introducing rotational polarization to the illumination beam. The illumination from the polarizer is directed onto the sample at a non-normal angle of incidence, and the non-normal-incidence reflectance data results from this illumination from the second light source. The sample reflects a portion of the non-normal-incident illumination light to a focusing lens 3e, which focuses the non-normal-incidence reflected light for collection by an angular reflectance collection fiber 4e.

The angled reflectance data is used with the normal-incidence reflectance data and the transmittance data in a model-free method or application to determine a number of properties of the film. These properties include the film thickness (d), roughness, and composition. The composition, which may be homogenous or not, is usually described in terms of the optical constants of refractive index (n) and extinction coefficient (k). Both n and k are functions of wavelength, which means that, when measured, they are determined for each discrete wavelength that comprises the SR spectrum.

Figure 5:
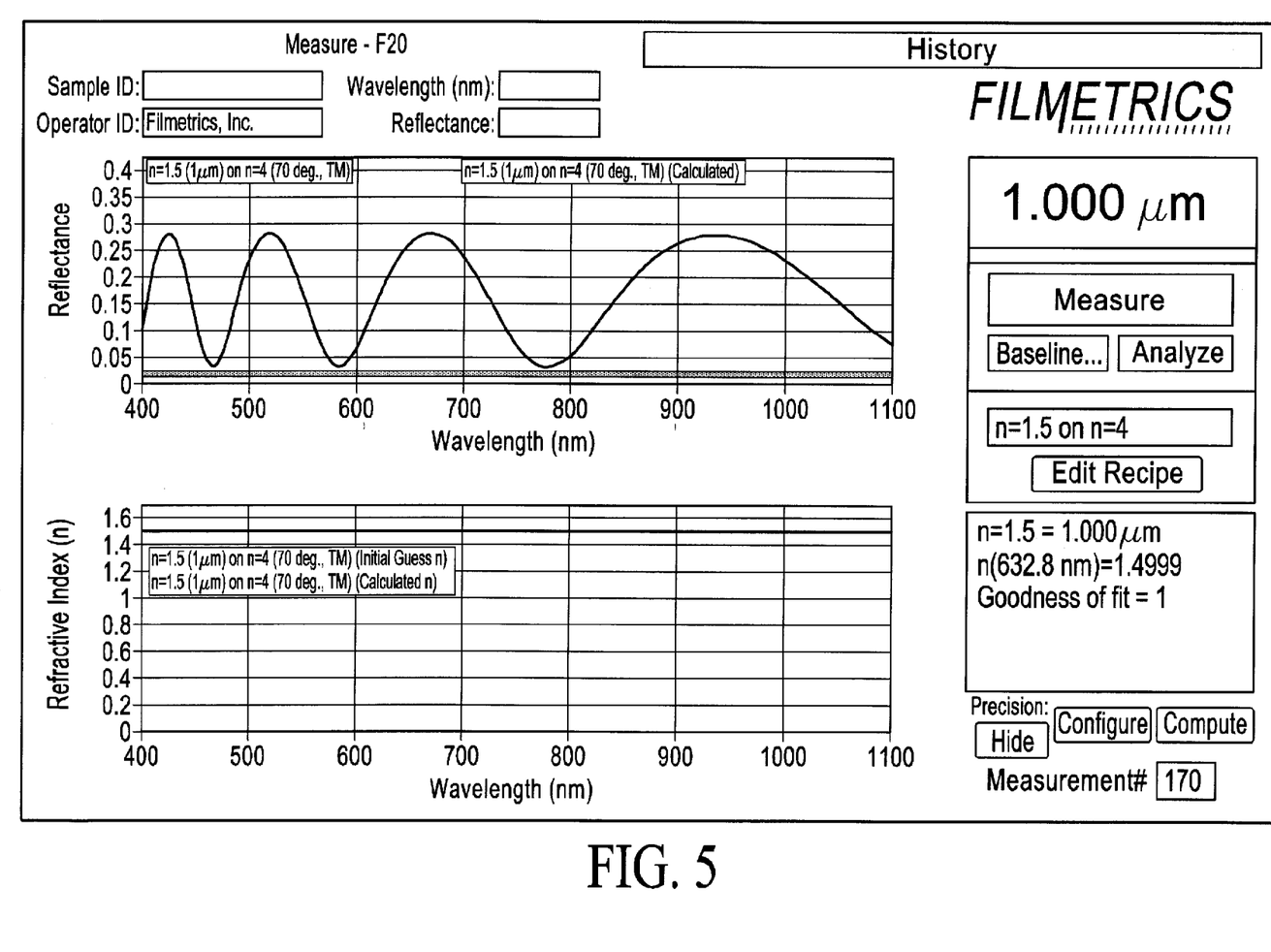
FIG. 5 shows the calculated 70-degree from normal-incidence TM reflectance spectra of a 1 um-thick n=1.5 film on an n=4 substrate.

FIG. 5 shows the AR of the film stack of FIGS. 2 and 3, with the incident beam at 70 degrees from normal and TM polarized, under an embodiment. Note that there are fewer oscillations in this spectrum than in the normal incidence R of FIG.

2, but otherwise the two spectra look qualitatively similar. However, it is instructive to see how the AR spectrum would look under the n and d solution found in FIG. 3, so this is shown in FIG. 6.

Figure 6:
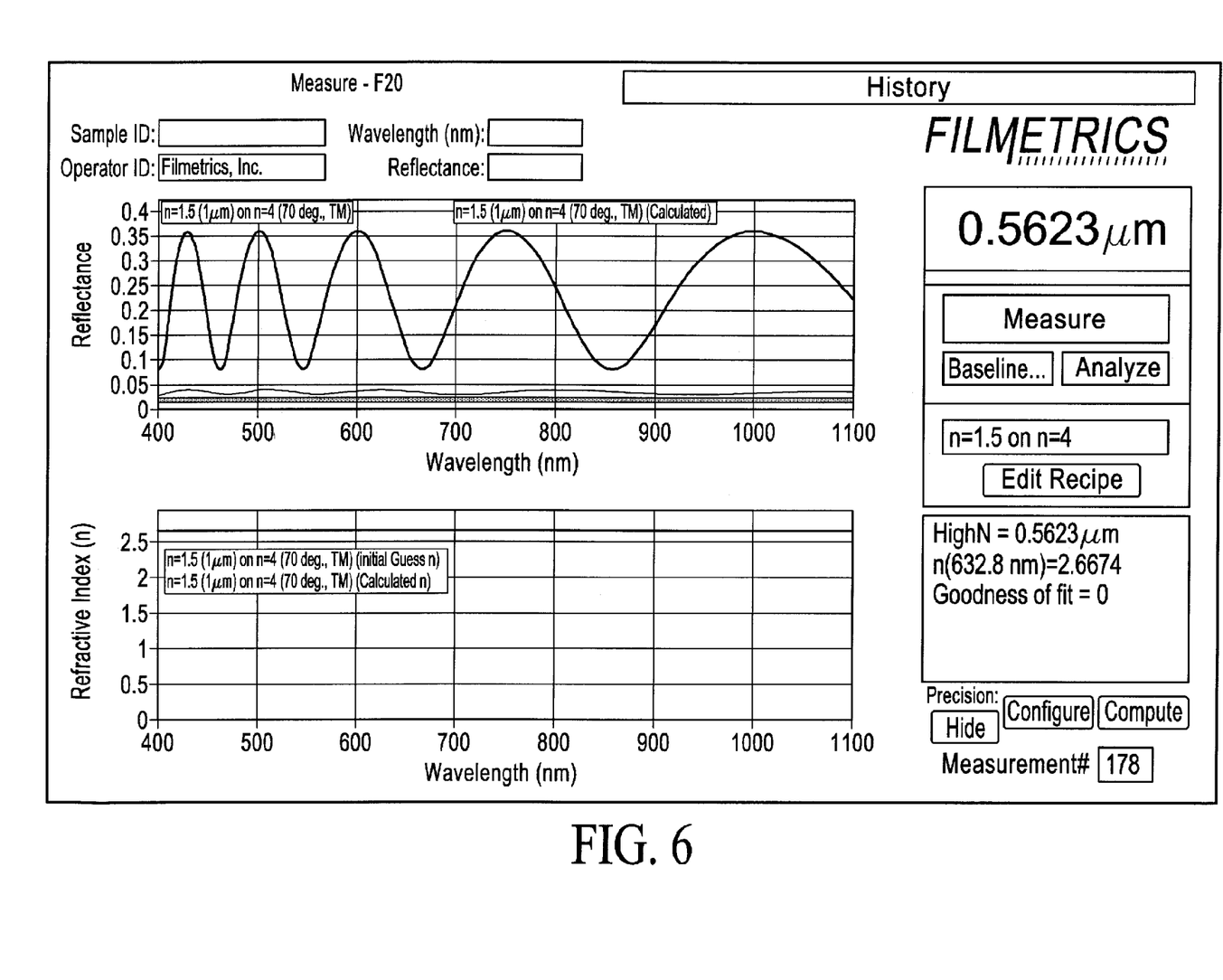
FIG. 6 shows the calculated 70-degree from normal-incidence TM reflectance spectra of a 1 um-thick n=1.5 film on an n=4 substrate, along with the calculated 70-degree from normal-incidence TM reflectance spectra of a 0.5623 um-thick n=2.6674 film on an n=4 substrate.

FIG. 6 shows that the second normal-incidence R solution found and shown in FIG. 3 (n=2.6674 and d=0.5623) results in a completely different AR spectrum that the theoretical spectrum shown in FIG. 3 (actually under the simulated spectrum in that figure), under an embodiment. Therefore, by the addition of the AR data, it can be concluded that the second R solution is invalid, resulting in there being only one unique solution.

That adding AR data to the R and T data results in a unique model-free solution for n, k, and d for smooth homogenous single-layer films can be understood by considering the number of parameters involved, similar to the process described above. In this case there are 3i known parameters (i for each of R, T, and AR) and 2i +1 unknown parameters (n, k, and d), so that the number of known parameters is greater than or equal to the number of unknown parameters, even when i=1.

Similarly, if the film sample is more complicated and has more than 3i unknown parameters, combining AR data with R and T data will result in a more robust solution than by using R and T alone.

The measurement of T implies that the substrate is transparent, thus backside reflections are present and the degree that they are collected by the detection optics must be accounted for during AR. However, this is a situation commonly encountered in ellipsometry, and those skilled in the art will be aware of beam aperturing and other techniques used to deal with this issue.

While the embodiment described above uses the angled reflectance (AR) data in combination with both the normal-incidence reflectance data and the transmittance data, the embodiment is not so limited. Consequently, alternative embodiments use the angled reflectance data in combination with either the normal-incidence reflectance data or the transmittance data. These alternative embodiments are described in detail below.

A measurement system of an alternative embodiment uses normal-incidence reflectance data and angled reflectance data to determine the properties of the film. The system of this alternative embodiment includes a first light source that illuminates a film with first illumination having a first angle of incidence that is approximately normal to the film, and a first collection fiber that collects reflected light of the first illumination reflected by the film. The system also includes a second light source that illuminates the film with second illumination having a second angle of incidence that is approximately non-normal to the film. A second collection fiber collects reflected light of the second illumination reflected by the film.

The spectral reflectance measuring method of this alternative embodiment comprises illuminating a film from a first angle of incidence that is approximately normal to the film and collecting normal-incidence reflected light from the film. Further, the film is illuminated from a second angle of incidence that is approximately non-normal to the film and collecting non-normal-incidence reflected light from the film. The method determines properties of the film using data of the normal-incidence reflected light and the non-normal-incidence reflected light.

The system of this alternative embodiment is similar to the system shown and described above with reference to FIG. 4 except it does not make use of transmittance data and, thus, may not include the focusing lens 3c and the transmittance collection fiber 4c. More specifically, the apparatus includes the first light source 4a. The light from the first light source 4a is collimated by a lens 3a, and directed by a beamsplitter 2 onto the sample 1. The sample reflects a portion of the normal-incident illumination light back down through the beamsplitter 2 to a focusing lens 3b. The focusing lens 3b focuses the normal-incidence reflected light for collection by a reflectance collection fiber 4b.

The apparatus also includes the second light source 4d. The light from the second light source 4d is collimated by a lens 3d and then directed to a polarizer 5 that polarizes the incident illumination light so that the electric field components are either parallel (TM polarized) or perpendicular (TE polarized) to the sample surface. The illumination from the polarizer is directed onto the sample at a non-normal angle of incidence, and the non-normal-incidence reflectance data results from this illumination from the second light source. The sample reflects a portion of the non-normal-incident illumination light to a focusing lens 3e, which focuses the non-normal-incidence reflected light for collection by an angular reflectance collection fiber 4e. In this alternative embodiment, the angled reflectance data is used only with the normal-incidence reflectance data in a model-free process or application to determine a number of properties of the film, properties that include but are not limited to the film thickness (d), the refractive index (n), and the extinction coefficient (k).

A measurement system of another alternative embodiment uses transmittance data and angled reflectance data to determine the properties of the film. The system of this alternative embodiment includes a first light source that illuminates a film with first illumination having a first angle of incidence that is approximately normal to the film, and a first collection fiber that collects transmitted light of the first illumination transmitted by the film. The system also includes a second light source that illuminates the film with second illumination having a second angle of incidence that is approximately non-normal to the film, and a second collection fiber that collects reflected light of the second illumination reflected by the film.

The spectral reflectance measuring method of this additional alternative embodiment comprises illuminating a film from a first angle of incidence that is approximately normal to the film and collecting normal-incidence transmitted light transmitted by the film. Additionally, the method includes illuminating the film from a second angle of incidence that is approximately non-normal to the film and collecting non-normal-incidence reflected light from the film. Properties of the film are determined using data of the normal-incidence transmitted light and the non-normal-incidence reflected light.

The system of this other alternative embodiment is similar to the system shown and described above with reference to FIG. 4 except it does not make use of normal-incidence reflectance data and, thus, may not include the focusing lens 3b and the reflectance collection fiber 4b. More specifically, the apparatus includes a first light source 4a, and the light from the first light source 4a is collimated by a lens 3a, and directed by a beamsplitter 2 onto the sample 1. Any portion of the non-reflected light that illuminates the sample is transmitted through the sample to focusing lens 3c, which focuses the transmitted light for collection by a transmittance collection fiber 4c.

The apparatus also includes a second light source 4d that is, for example, an optical fiber 4d. The light from the second light source 4d is collimated by a lens 3d and then directed to a polarizer 5 where it is polarized so that the electric field components are either parallel (TM polarized) or perpendicular (TE polarized) to the sample surface, thus preventing the sample from introducing rotational polarization to the illumination beam. The illumination from the polarizer is directed onto the sample at a non-normal angle of incidence, and the non-normal-incidence reflectance data results from this illumination from the second light source. The sample reflects a portion of the non-normal-incident illumination light to a focusing lens 3e, which focuses the non-normal-incidence reflected light for collection by an angular reflectance collection fiber 4e. In this additional alternative embodiment, the angled reflectance data is used only with the transmittance data in a model-free process or application to determine a number of properties of the film, properties that include but are not limited to the film thickness (d), the refractive index (n), and the extinction coefficient (k).

The principles described herein are applicable to angled transmittance measurements (AT), but AT is less practical than AR because the entire transmitted beam is shifted laterally by the substrate and can substantially or entirely miss the collection optics. Therefore, the discussion herein has used AR for illustration.

Embodiments described herein include a spectral reflectance system, comprising a first light source that illuminates a film with first illumination having a first angle of incidence that is approximately normal to the film. The film covers at least a portion of a first side of a sample. The system includes a transmittance collection fiber that collects transmitted light of the first illumination transmitted by the film The system includes a first collection fiber that collects reflected light of the first illumination reflected by the film. The system includes a second light source that illuminates the film with second illumination having a second angle of incidence that is approximately non-normal to the film. The system includes a second collection fiber that collects reflected light of the second illumination reflected by the film.

Embodiments described herein include a spectral reflectance system, comprising: a first light source that illuminates a film with first illumination having a first angle of incidence that is approximately normal to the film, wherein the film covers at least a portion of a first side of a sample; a transmittance collection fiber that collects transmitted light of the first illumination transmitted by the film; a first collection fiber that collects reflected light of the first illumination reflected by the film; a second light source that illuminates the film with second illumination having a second angle of incidence that is approximately non-normal to the film; and a second collection fiber that collects reflected light of the second illumination reflected by the film.

The system comprises a beamsplitter positioned to direct the first illumination from the first light source to the film.

The beamsplitter of an embodiment is positioned to direct the reflected light of the first illumination from the film to the first collection fiber.

The system comprises a first lens positioned between the first light source and the beamsplitter, wherein the first lens is a collimating lens.

The system comprises a second lens positioned between the beamsplitter and the first collection fiber, wherein the second lens is a focusing lens.

The system comprises a third lens positioned between the sample and the transmittance collection fiber, wherein the third lens is a focusing lens.

The system comprises a fourth lens positioned between the second light source and the sample, wherein the fourth lens is a collimating lens.

The system comprises a fifth lens positioned between the sample and the second collection fiber, wherein the fifth lens is a focusing lens.

The system comprises a polarizer positioned between the second light source and the sample, wherein the polarizer polarizes the second illumination.

The polarizer of an embodiment polarizes the second illumination so that electric field components of the second illumination are parallel to the film.

The polarizer of an embodiment polarizes the second illumination so that electric field components of the second illumination are perpendicular to the film.

The first illumination and the second illumination of an embodiment are directed at the film.

The system comprises a processor executing a model-free application, wherein the model-free application determines at least one property of the film using data of the normal-incidence reflected light, the normal-incidence transmitted light, and the non-normal-incidence reflected light.

The at least one property of an embodiment is refractive index of the film.

The at least one property of an embodiment is extinction coefficient of the film.

The at least one property of an embodiment is thickness of the film.

The at least one property of an embodiment is one or more of refractive index, extinction coefficient, and thickness of the film.

Embodiments described herein include a method for measuring spectral reflectance. The method comprises illuminating a film from a first angle of incidence that is approximately normal to the film and collecting normal-incidence reflected light from the film and normal-incidence transmitted light transmitted by the film. The film covers at least a portion of a first side of a sample. The method comprises illuminating the film from a second angle of incidence that is approximately non-normal to the film and collecting non-normal-incidence reflected light from the film. The method comprises determining at least one property of the film using data of the normal-incidence reflected light, the normal-incidence transmitted light, and the non-normal-incidence reflected light.

Embodiments described herein include a method for measuring spectral reflectance, the method comprising: illuminating a film from a first angle of incidence that is approximately normal to the film and collecting normal-incidence reflected light from the film and normal-incidence transmitted light transmitted by the film, wherein the film covers at least a portion of a first side of a sample; illuminating the film from a second angle of incidence that is approximately non-normal to the film and collecting non-normal-incidence reflected light from the film; and determining at least one property of the film using data of the normal-incidence reflected light, the normal-incidence transmitted light, and the non-normal-incidence reflected light.

The illuminating of the film of an embodiment from a second angle of incidence comprises illuminating with polarized light.

The polarized light of an embodiment comprises electric field components that are parallel to a surface of the film.

The polarized light of an embodiment comprises electric field components that are perpendicular to a surface of the film.

The determining of the at least one property of the film of an embodiment comprises using a model-free application, wherein the model-free application determines the at least one property.

The at least one property of the film of an embodiment comprises at least one optical constant.

The at least one property of an embodiment is refractive index of the film.

The at least one property of an embodiment is extinction coefficient of the film.

The at least one property of an embodiment is thickness of the film.

The at least one property of an embodiment is one or more of refractive index, extinction coefficient, and thickness of the film.

Embodiments described herein include a spectral reflectance system, comprising a first light source that illuminates a film with first illumination having a first angle of incidence that is approximately normal to the film. The film covers at least a portion of a first side of a sample. The system includes a first collection fiber that collects reflected light of the first illumination reflected by the film. The system includes a second light source that illuminates the film with second illumination having a second angle of incidence that is approximately non-normal to the film. The system includes a second collection fiber that collects reflected light of the second illumination reflected by the film.

Embodiments described herein include a spectral reflectance system, comprising: a first light source that illuminates a film with first illumination having a first angle of incidence that is approximately normal to the film, wherein the film covers at least a portion of a first side of a sample; a first collection fiber that collects reflected light of the first illumination reflected by the film; a second light source that illuminates the film with second illumination having a second angle of incidence that is approximately non-normal to the film; and a second collection fiber that collects reflected light of the second illumination reflected by the film.

The system comprises a beamsplitter positioned to direct the first illumination from the first light source to the film.

The beamsplitter of an embodiment is positioned to direct the reflected light of the first illumination from the film to the first collection fiber.

The system comprises a first lens positioned between the first light source and the beamsplitter, wherein the first lens is a collimating lens.

The system comprises a second lens positioned between the beamsplitter and the first collection fiber, wherein the second lens is a focusing lens.

The system comprises a third lens positioned between the second light source and the sample, wherein the third lens is a collimating lens.

The system comprises a fourth lens positioned between the sample and the second collection fiber, wherein the fourth lens is a focusing lens.

The system comprises a polarizer positioned between the second light source and the sample, wherein the polarizer polarizes the second illumination.

The polarizer of an embodiment polarizes the second illumination so that electric field components of the second illumination are parallel to the film.

The polarizer of an embodiment polarizes the second illumination so that electric field components of the second illumination are perpendicular to the film.

The first illumination and the second illumination of an embodiment are directed at the film.

The system comprises a processor executing a model-free application, wherein the model-free application determines at least one property of the film using data of the reflected light of the first illumination and the reflected light of the second illumination.

The at least one property of an embodiment is refractive index of the film.

The at least one property of an embodiment is extinction coefficient of the film.

The at least one property of an embodiment is thickness of the film.

The at least one property of an embodiment is one or more of refractive index, extinction coefficient, and thickness of the film.

Embodiments described herein include a method for measuring spectral reflectance. The method comprises illuminating a film from a first angle of incidence that is approximately normal to the film and collecting normal-incidence reflected light from the film. The film covers at least a portion of a first side of a sample. The method comprises illuminating the film from a second angle of incidence that is approximately non-normal to the film and collecting non-normal-incidence reflected light from the film. The method comprises determining properties of the film using data of the normal-incidence reflected light and the non-normal-incidence reflected light.

Embodiments described herein include a method for measuring spectral reflectance, the method comprising: illuminating a film from a first angle of incidence that is approximately normal to the film and collecting normal-incidence reflected light from the film, wherein the film covers at least a portion of a first side of a sample; illuminating the film from a second angle of incidence that is approximately non-normal to the film and collecting non-normal-incidence reflected light from the film; and determining properties of the film using data of the normal-incidence reflected light and the non-normal-incidence reflected light.

The illuminating of the film from a second angle of incidence of an embodiment comprises illuminating with polarized light.

The polarized light of an embodiment comprises electric field components that are parallel to a surface of the film.

The polarized light of an embodiment comprises electric field components that are perpendicular to a surface of the film.

The determining of the at least one property of the film of an embodiment comprises using a model-free application, wherein the model-free application determines the at least one property.

The at least one property of the film of an embodiment comprises at least one optical constant of the film.

The at least one property of an embodiment is extinction coefficient of the film.

The at least one property of an embodiment is thickness of the film.

The at least one property of an embodiment is one or more of refractive index, extinction coefficient, and thickness of the film.

Embodiments described herein include a spectral reflectance system, comprising a first light source that illuminates a film with first illumination having a first angle of incidence that is approximately normal to the film. The film covers at least a portion of a first side of a sample. The system includes a first collection fiber that collects transmitted light of the first illumination transmitted by the film. The system includes a second light source that illuminates the film with second illumination having a second angle of incidence that is approximately non-normal to the film. The system includes a second collection fiber that collects reflected light of the second illumination reflected by the film.

Embodiments described herein include a spectral reflectance system, comprising: a first light source that illuminates a film with first illumination having a first angle of incidence that is approximately normal to the film, wherein the film covers at least a portion of a first side of a sample; a first collection fiber that collects transmitted light of the first illumination transmitted by the film; a second light source that illuminates the film with second illumination having a second angle of incidence that is approximately non-normal to the film; and a second collection fiber that collects reflected light of the second illumination reflected by the film.

The system comprises a beamsplitter positioned to direct the first illumination from the first light source to the film.

The system comprises a first lens positioned between the first light source and the beamsplitter, wherein the first lens is a collimating lens.

The system comprises a second lens positioned between the sample and the first collection fiber, wherein the second lens is a focusing lens.

The system comprises a third lens positioned between the second light source and the sample, wherein the third lens is a collimating lens.

The system comprises a fourth lens positioned between the sample and the second collection fiber, wherein the fourth lens is a focusing lens.

The system comprises a polarizer positioned between the second light source and the sample, wherein the polarizer polarizes the second illumination.

The polarizer of an embodiment polarizes the second illumination so that electric field components of the second illumination are parallel to the film.

The polarizer of an embodiment polarizes the second illumination so that electric field components of the second illumination are perpendicular to the film.

The system comprises a processor executing a model-free application, wherein the model-free application determines at least one property of the film using data of the normal-incidence transmitted light and the non-normal-incidence reflected light.

The at least one property of an embodiment is refractive index of the film.

The at least one property of an embodiment is extinction coefficient of the film.

The at least one property of an embodiment is thickness of the film.

The at least one property of an embodiment is one or more of refractive index, extinction coefficient, and thickness of the film.

Embodiments described herein include a method for measuring spectral reflectance. The method comprises illuminating a film from a first angle of incidence that is approximately normal to the film and collecting normal-incidence transmitted light transmitted by the film. The film covers at least a portion of a first side of a sample. The method comprises illuminating the film from a second angle of incidence that is approximately non-normal to the film and collecting non-normal-incidence reflected light from the film. The method comprises determining properties of the film using data of the normal-incidence transmitted light and the non-normal-incidence reflected light.

Embodiments described herein include a method for measuring spectral reflectance, the method comprising: illuminating a film from a first angle of incidence that is approximately normal to the film and collecting normal-incidence transmitted light transmitted by the film, wherein the film covers at least a portion of a first side of a sample; illuminating the film from a second angle of incidence that is approximately non-normal to the film and collecting non-normal-incidence reflected light from the film; and determining properties of the film using data of the normal-incidence transmitted light and the non-normal-incidence reflected light.

The illuminating of the film from a second angle of incidence of an embodiment comprises illuminating with polarized light.

The polarized light of an embodiment comprises electric field components that are parallel to a surface of the film.

The polarized light of an embodiment comprises electric field components that are perpendicular to a surface of the film.

The determining of the at least one property of the film of an embodiment comprises using a model-free application, wherein the model-free application determines the at least one property.

The at least one property of the film of an embodiment comprises at least one optical constant.

The at least one property of an embodiment is refractive index of the film.

The at least one property of an embodiment is extinction coefficient of the film.

The at least one property of an embodiment is thickness of the film.

The at least one property of an embodiment is one or more of refractive index, extinction coefficient, and thickness of the film.

Unless the context clearly requires otherwise, throughout the description, the words "comprise," "comprising," and the like are to be construed in an inclusive sense as opposed to an exclusive or exhaustive sense; that is to say, in a sense of "including, but not limited to." Words using the singular or plural number also include the plural or singular number respectively. Additionally, the words "herein," "hereunder," "above," "below," and words of similar import refer to this application as a whole and not to any particular portions of this application. When the word "or" is used in reference to a list of two or more items, that word covers all of the following interpretations of the word: any of the items in the list, all of the items in the list and any combination of the items in the list.

The above description of embodiments of the reflectance systems and methods is not intended to be exhaustive or to limit the systems and methods described to the precise form disclosed. While specific embodiments of, and examples for, the reflectance systems and methods are described herein for illustrative purposes, various equivalent modifications are possible within the scope of other reflectance systems and methods, as those skilled in the relevant art will recognize. The teachings of the reflectance systems and methods provided herein can be applied to other processing and measurement systems and methods, not only for the systems and methods described above.

The elements and acts of the various embodiments described above can be combined to provide further embodiments. These and other changes can be made to the reflectance systems and methods in light of the above detailed description.

In general, in the following claims, the terms used should not be construed to limit the reflectance systems and methods to the specific embodiments disclosed in the specification and the claims, but should be construed to include all systems and methods that operate under the claims. Accordingly, the reflectance systems and methods are not limited by the disclosure, but instead the scope of the reflectance systems and methods is to be determined entirely by the claims.

While certain aspects of the reflectance systems and methods are presented below in certain claim forms, the inventors contemplate the various aspects of the reflectance systems and methods in any number of claim forms. Accordingly, the inventors reserve the right to add additional claims after filing the application to pursue such additional claim forms for other aspects of the reflectance systems and methods.

What is claimed is:

1. A spectral reflectance system, comprising:
a first light source that illuminates a film with first illumination having a first angle of incidence that is approximately normal to the film, wherein the film covers at least a portion of a first side of a sample;
a transmittance collection fiber that collects transmitted light of the first illumination transmitted by the film;
a first collection fiber that collects reflected light of the first illumination reflected by the film;
a second light source that illuminates the film with second illumination having a second angle of incidence that is approximately non-normal to the film;
a second collection fiber that collects reflected light of the second illumination reflected by the film; and
a processor executing a model-free application that determines at least one property of the film using data of the normal-incidence reflected light, the normal-incidence transmitted light, and the non-normal-incidence reflected light.

2. The spectral reflectance system of claim 1, comprising a beamsplitter positioned to direct the first illumination from the first light source to the film.

3. The spectral reflectance system of claim 2, wherein the beamsplitter is positioned to direct the reflected light of the first illumination from the film to the first collection fiber.

4. The spectral reflectance system of claim 2, comprising a first lens positioned between the first light source and the beamsplitter, wherein the first lens is a collimating lens.

5. The spectral reflectance system of claim 2, comprising a second lens positioned between the beamsplitter and the first collection fiber, wherein the second lens is a focusing lens.

6. The spectral reflectance system of claim 1, comprising a third lens positioned between the sample and the transmittance collection fiber, wherein the third lens is a focusing lens.

7. The spectral reflectance system of claim 1, comprising a fourth lens positioned between the second light source and the sample, wherein the fourth lens is a collimating lens.

8. The spectral reflectance system of claim 1, comprising a fifth lens positioned between the sample and the second collection fiber, wherein the fifth lens is a focusing lens.

9. The spectral reflectance system of claim 1, comprising a polarizer positioned between the second light source and the sample, wherein the polarizer polarizes the second illumination.

10. The spectral reflectance system of claim 9, wherein the polarizer polarizes the second illumination so that electric field components of the second illumination are parallel to the film.

11. The spectral reflectance system of claim 9, wherein the polarizer polarizes the second illumination so that electric field components of the second illumination are perpendicular to the film.

12. The spectral reflectance system of claim 1, wherein the first illumination and the second illumination are directed at the film.

13. The spectral reflectance system of claim 1, wherein the at least one property is refractive index of the film.

14. The spectral reflectance system of claim 1, wherein the at least one property is extinction coefficient of the film.

15. The spectral reflectance system of claim 1, wherein the at least one property is thickness of the film.

16. The spectral reflectance system of claim 1, wherein the at least one property is one or more of refractive index, extinction coefficient, and thickness of the film.

17. A method for measuring spectral reflectance, the method comprising:
illuminating a film from a first angle of incidence that is approximately normal to the film and collecting normal-incidence reflected light from the film and normal-incidence transmitted light transmitted by the film, wherein the film covers at least a portion of a first side of a sample;
illuminating the film from a second angle of incidence that is approximately non-normal to the film and collecting non-normal-incidence reflected light from the film; and
determining at least one property of the film using a model-free application and data of the normal-incidence reflected light, the normal-incidence transmitted light, and the non-normal-incidence reflected light.

18. The method of claim 17, wherein the illuminating of the film from a second angle of incidence comprises illuminating with polarized light.

19. The method of claim 18, wherein the polarized light comprises electric field components that are parallel to a surface of the film.

20. The method of claim 18, wherein the polarized light comprises electric field components that are perpendicular to a surface of the film.

21. The method of claim 17, wherein the at least one property of the film comprises at least one optical constant.

22. The method of claim 17, wherein the at least one property is refractive index of the film.

23. The method of claim 17, wherein the at least one property is extinction coefficient of the film.

24. The method of claim 17, wherein the at least one property is thickness of the film.

25. The method of claim 17, wherein the at least one property is one or more of refractive index, extinction coefficient, and thickness of the film.

26. A spectral reflectance system, comprising:
a first light source that illuminates a film with first illumination having a first angle of incidence that is approximately normal to the film, wherein the film covers at least a portion of a first side of a sample;
a first collection fiber that collects reflected light of the first illumination reflected by the film;
a second light source that illuminates the film with second illumination having a second angle of incidence that is approximately non-normal to the film;
a second collection fiber that collects reflected light of the second illumination reflected by the film; and
a processor executing a model-free application that determines at least one property of the film using data of the reflected light of the first illumination and the reflected light of the second illumination.

27. The spectral reflectance system of claim 26, comprising a beamsplitter positioned to direct the first illumination from the first light source to the film.

28. The spectral reflectance system of claim 27, wherein the beamsplitter is positioned to direct the reflected light of the first illumination from the film to the first collection fiber.

29. The spectral reflectance system of claim 27, comprising a first lens positioned between the first light source and the beamsplitter, wherein the first lens is a collimating lens.

30. The spectral reflectance system of claim 27, comprising a second lens positioned between the beamsplitter and the first collection fiber, wherein the second lens is a focusing lens.

31. The spectral reflectance system of claim 26, comprising a third lens positioned between the second light source and the sample, wherein the third lens is a collimating lens.

32. The spectral reflectance system of claim 26, comprising a fourth lens positioned between the sample and the second collection fiber, wherein the fourth lens is a focusing lens.

33. The spectral reflectance system of claim 26, comprising a polarizer positioned between the second light source and the sample, wherein the polarizer polarizes the second illumination.

34. The spectral reflectance system of claim 33, wherein the polarizer polarizes the second illumination so that electric field components of the second illumination are parallel to the film.

35. The spectral reflectance system of claim 33, wherein the polarizer polarizes the second illumination so that electric field components of the second illumination are perpendicular to the film.

36. The spectral reflectance system of claim 26, wherein the first illumination and the second illumination are directed at the film.

37. The spectral reflectance system of claim 26, wherein the at least one property is refractive index of the film.

38. The spectral reflectance system of claim 26, wherein the at least one property is extinction coefficient of the film.

39. The spectral reflectance system of claim 26, wherein the at least one property is thickness of the film.

40. The spectral reflectance system of claim 26, wherein the at least one property is one or more of refractive index, extinction coefficient, and thickness of the film.

41. A method for measuring spectral reflectance, the method comprising:
    illuminating a film from a first angle of incidence that is approximately normal to the film and collecting normal-incidence reflected light from the film, wherein the film covers at least a portion of a first side of a sample;
    illuminating the film from a second angle of incidence that is approximately non-normal to the film and collecting non-normal-incidence reflected light from the film; and
    determining properties of the film using a model-free application and data of the normal-incidence reflected light and the non-normal-incidence reflected light.

42. The method of claim 41, wherein the illuminating of the film from a second angle of incidence comprises illuminating with polarized light.

43. The method of claim 42, wherein the polarized light comprises electric field components that are parallel to a surface of the film.

44. The method of claim 42, wherein the polarized light comprises electric field components that are perpendicular to a surface of the film.

45. The method of claim 41, wherein the at least one property of the film comprises at least one optical constant of the film.

46. The method of claim 41, wherein the at least one property is extinction coefficient of the film.

47. The method of claim 41, wherein the at least one property is thickness of the film.

48. The method of claim 41, wherein the at least one property is one or more of refractive index, extinction coefficient, and thickness of the film.

49. A spectral reflectance system, comprising:
    a first light source that illuminates a film with first illumination having a first angle of incidence that is approximately normal to the film, wherein the film covers at least a portion of a first side of a sample;
    a first collection fiber that collects transmitted light of the first illumination transmitted by the film;
    a second light source that illuminates the film with second illumination having a second angle of incidence that is approximately non-normal to the film;
    a second collection fiber that collects reflected light of the second illumination reflected by the film; and
    a processor executing a model-free application, wherein the model-free application determines at least one property of the film using data of the normal-incidence transmitted light and the non-normal-incidence reflected light.

50. The spectral reflectance system of claim 49, comprising a beamsplitter positioned to direct the first illumination from the first light source to the film.

51. The spectral reflectance system of claim 50, comprising a first lens positioned between the first light source and the beamsplitter, wherein the first lens is a collimating lens.

52. The spectral reflectance system of claim 49, comprising a second lens positioned between the sample and the first collection fiber, wherein the second lens is a focusing lens.

53. The spectral reflectance system of claim 49, comprising a third lens positioned between the second light source and the sample, wherein the third lens is a collimating lens.

54. The spectral reflectance system of claim 49, comprising a fourth lens positioned between the sample and the second collection fiber, wherein the fourth lens is a focusing lens.

55. The spectral reflectance system of claim 49, comprising a polarizer positioned between the second light source and the sample, wherein the polarizer polarizes the second illumination.

56. The spectral reflectance system of claim 55, wherein the polarizer polarizes the second illumination so that electric field components of the second illumination are parallel to the film.

57. The spectral reflectance system of claim 55, wherein the polarizer polarizes the second illumination so that electric field components of the second illumination are perpendicular to the film.

58. The spectral reflectance system of claim 49, wherein the at least one property is refractive index of the film.

59. The spectral reflectance system of claim 49, wherein the at least one property is extinction coefficient of the film.

60. The spectral reflectance system of claim 49, wherein the at least one property is thickness of the film.

61. The spectral reflectance system of claim 49, wherein the at least one property is one or more of refractive index, extinction coefficient, and thickness of the film.

62. A method for measuring spectral reflectance, the method comprising:
    illuminating a film from a first angle of incidence that is approximately normal to the film and collecting normal-incidence transmitted light transmitted by the film, wherein the film covers at least a portion of a first side of a sample;
    illuminating the film from a second angle of incidence that is approximately non-normal to the film and collecting non-normal-incidence reflected light from the film; and
    determining properties of the film using a model-free application and data of the normal-incidence transmitted light and the non-normal-incidence reflected light.

63. The method of claim 62, wherein the illuminating of the film from a second angle of incidence comprises illuminating with polarized light.

64. The method of claim 63, wherein the polarized light comprises electric field components that are parallel to a surface of the film.

65. The method of claim 63, wherein the polarized light comprises electric field components that are perpendicular to a surface of the film.

66. The method of claim 62, wherein the at least one property of the film comprises at least one optical constant.

67. The method of claim 62, wherein the at least one property is refractive index of the film.

68. The method of claim 62, wherein the at least one property is extinction coefficient of the film.

69. The method of claim 62, wherein the at least one property is thickness of the film.

70. The method of claim 62, wherein the at least one property is one or more of refractive index, extinction coefficient, and thickness of the film.

* * * * *